United States Patent
Eliason et al.

(10) Patent No.: US 9,474,486 B2
(45) Date of Patent: Oct. 25, 2016

(54) BASKET FOR A MULTI-ELECTRODE ARRAY CATHETER

(71) Applicant: St. Jude Medical, Atrial Fibrillation Division, Inc., St. Paul, MN (US)

(72) Inventors: Braden J. Eliason, Shoreview, MN (US); Don Curtis Deno, Andover, MN (US); Eric Jon Voth, Maplewood, MN (US); Dale Eric Just, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/790,110

(22) Filed: Mar. 8, 2013

(65) Prior Publication Data

US 2014/0257069 A1   Sep. 11, 2014

(51) Int. Cl.
| | | |
|---|---|---|
| *A61B 5/042* | (2006.01) | |
| *A61B 5/00* | (2006.01) | |
| *A61B 18/14* | (2006.01) | |
| *A61B 18/00* | (2006.01) | |

(52) U.S. Cl.
CPC .......... *A61B 5/6858* (2013.01); *A61B 5/0422* (2013.01); *A61B 18/1492* (2013.01); *A61B 2018/00267* (2013.01); *A61B 2018/00279* (2013.01); *A61B 2018/1435* (2013.01)

(58) Field of Classification Search
CPC  A61B 5/0422; A61B 5/6858; A61B 5/6859; A61B 18/1492; A61N 1/056
USPC .................................. 600/374, 381; 606/41
See application file for complete search history.

(56) References Cited

U.S. PATENT DOCUMENTS

| | | | |
|---|---|---|---|
| 4,299,225 A | | 11/1981 | Glassman |
| 4,699,147 A | * | 10/1987 | Chilson et al. ............... 600/374 |
| 5,311,866 A | * | 5/1994 | Kagan et al. .................. 600/374 |
| 5,345,936 A | | 9/1994 | Pomeranz et al. |
| 5,549,661 A | | 8/1996 | Kordis et al. |
| 5,782,239 A | * | 7/1998 | Webster, Jr. .................. 600/374 |

(Continued)

FOREIGN PATENT DOCUMENTS

| | | |
|---|---|---|
| JP | H08501477 A | 2/1996 |
| JP | H11501554 A | 2/1999 |

(Continued)

OTHER PUBLICATIONS

U.S. Appl. No. 13/340,760.

(Continued)

*Primary Examiner* — Lee S Cohen
(74) *Attorney, Agent, or Firm* — Dykema Gossett, PLLC.

(57) ABSTRACT

An electrophysiology catheter is provided. In one embodiment, the catheter includes an elongate, deformable shaft having a proximal end and a distal end and a basket electrode assembly coupled to the distal end of the shaft. The basket electrode assembly has a proximal end and a distal end and is configured to assume a compressed state and an expanded state. The electrode assembly further includes one or more tubular splines having a plurality of electrodes disposed thereon and a plurality of conductors. Each of the plurality of conductors extends through the tubular spline from a corresponding one of the plurality of electrodes to the proximal end of the basket electrode assembly. The tubular splines are configured to assume a non-planar (e.g., a twisted or helical) shape in the expanded state.

21 Claims, 9 Drawing Sheets

(56) References Cited

U.S. PATENT DOCUMENTS

| | | | |
|---|---|---|---|
| 5,860,974 A * | 1/1999 | Abele | A61B 8/12 600/374 |
| 6,146,379 A * | 11/2000 | Fleischman et al. | 606/41 |
| 7,269,453 B2 * | 9/2007 | Mogul | 600/374 |
| 7,340,307 B2 * | 3/2008 | Maguire et al. | 607/41 |
| 8,157,796 B2 | 4/2012 | Collins et al. | |
| 8,167,845 B2 | 5/2012 | Wang et al. | |
| 8,224,416 B2 | 7/2012 | de la Rama et al. | |
| 2004/0187875 A1 | 9/2004 | He et al. | |
| 2011/0213231 A1 | 9/2011 | Hall et al. | |
| 2012/0143298 A1 | 6/2012 | Just et al. | |
| 2013/0289369 A1 * | 10/2013 | Margolis | A61B 5/145 600/309 |

FOREIGN PATENT DOCUMENTS

| | | |
|---|---|---|
| JP | 2007524439 A | 8/2007 |
| JP | 2009500052 A | 1/2009 |
| JP | 2012505047 A | 3/2013 |
| WO | 94/06349 | 3/1994 |
| WO | WO95/10322 A1 | 4/1995 |
| WO | WO02/087679 A2 | 11/2002 |

OTHER PUBLICATIONS

Japan Patent Office, Office Action, Aug. 9, 2016, 4 pgs., Japan.

* cited by examiner

BASKET FOR A MULTI-ELECTRODE ARRAY CATHETER

BACKGROUND a. Field

The present disclosure relates to electrophysiology catheters. In particular, the instant disclosure relates to an electrophysiology catheter that enables a more even distribution of electrodes both when the catheter is in contact with tissue and when the catheter is not in contact with tissue and, therefore, a more even sampling of electrical activity in the tissue.

b. Background

Electrophysiology (EP) mapping catheters are used to generate electrophysiology maps of tissue in a region of interest. The use of EP mapping data in the diagnosis and treatment of tissues within a body is well known. For example, EP maps of heart tissue can be used to guide ablation catheters which are used to convey an electrical stimulus to a region of interest within the heart and create tissue necrosis. Ablation catheters may be used to create necrosis in heart tissue to correct conditions such as atrial and ventricular arrhythmias (including, but not limited to, ectopic atrial tachycardia, atrial fibrillation, atrial flutter and ventricular tachycardias). In addition to guiding ablation catheters, EP maps can also be used to evaluate the effectiveness of ablation therapy, or locate ectopic sources or a critical isthmus An EP mapping catheter includes one or more electrodes at a distal end that sample electrical activity in tissue. Many EP mapping catheters having a relatively large number, or array, of electrodes to enable sampling over a relatively wide area of interest and reduce procedure time. Referring to FIG. 1, one type of EP mapping catheter 10 in use today includes a collapsible and expandable basket electrode assembly 12 disposed at the distal end of the catheter 10. The basket electrode assembly 12 assumes a compressed state as the catheter is maneuvered through an introducer sheath to a region of interest in the body and an expanded state once the catheter reaches the region of interest and emerges from the sheath. The basket electrode assembly 12 includes a plurality of splines 14 on which electrodes 16 are disposed. The splines 14 are coupled together at proximal and distal ends and bow outward (i.e. assume a bowed shape) when the basket assembly 12 is in an expanded state.

The foregoing discussion is intended only to illustrate the present field and should not be taken as a disavowal of claim scope.

BRIEF SUMMARY

The present disclosure relates to an electrophysiology catheter. In particular, the instant disclosure relates to an electrophysiology catheter that may enable a more even distribution of electrodes both when the catheter is in contact with tissue and when the catheter is not in contact with tissue and, therefore, a more even sampling of electrical activity in the tissue.

An electrophysiology catheter in accordance with at least one embodiment of the present teachings includes an elongate, deformable shaft having a proximal end and a distal end. The catheter further includes a basket electrode assembly coupled to the distal end of the shaft. The basket electrode assembly comprises a proximal end and a distal end and is configured to assume a compressed state and an expanded state. The basket electrode assembly includes a spline having a plurality of electrodes disposed thereon. The spline is configured to assume a non-planar shape in the expanded state. The spline may, for example, assume a twisted shape and, in particular, a helical shape.

An electrophysiology catheter in accordance with at least another embodiment of the present teachings includes an elongate, deformable shaft having a proximal end and a distal end. The catheter further includes a basket electrode assembly coupled to the distal end of the shaft. The basket electrode assembly comprises a proximal end and a distal end and is configured to assume a compressed state and an expanded state. The basket electrode assembly includes a plurality of first splines. Each of the plurality of first splines is configured to assume a shape other than a helical shape in the expanded state. The basket electrode assembly further includes a second spline. The second spline comprises an electrode disposed thereon and is configured to assume a helical shape in the expanded state.

An electrophysiology catheter in accordance with at least another embodiment of the present teachings includes an elongate, deformable shaft comprising a proximal end and a distal end. The catheter further includes a basket electrode assembly coupled to the distal end of the shaft. The basket electrode assembly comprises a proximal end and a distal end and a central longitudinal axis and is configured to assume a compressed state and an expanded state. The basket electrode assembly includes a first spline. The first spline comprises an electrode disposed thereon and comprises a first maximum radius relative to the axis in the expanded state. The basket electrode assembly further includes a second spline. The second spline comprises an electrode disposed thereon and comprises a second maximum radius relative to the axis in the expanded state. The second maximum radius is different than the first maximum radius.

An electrophysiology catheter in accordance with one or more of the present teachings may enable a more even distribution of electrodes both when the catheter is in contact with tissue and when the catheter is not in contact with tissue and, therefore, a more even sampling of electrical activity in the tissue.

The foregoing and other aspects, features, details, utilities, and advantages of the present disclosure will be apparent from reading the following description and claims, and from reviewing the accompanying drawings.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 2:
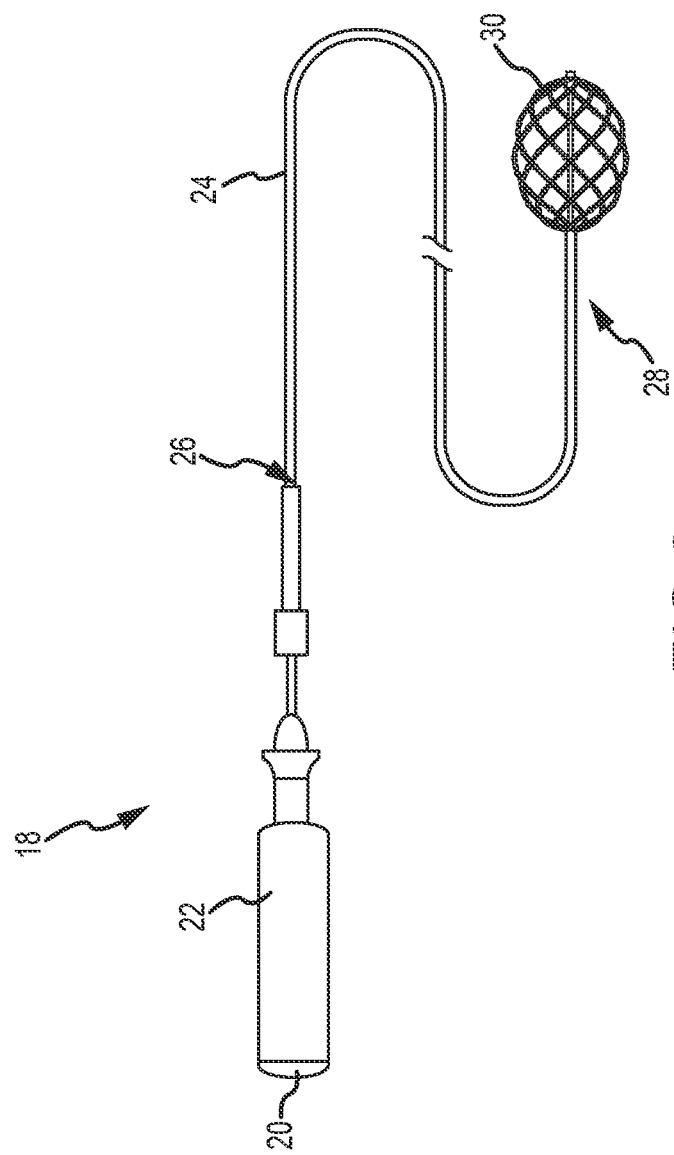
FIG. 2 is a perspective view of an electrophysiology catheter in accordance with one embodiment of the present teachings.

Referring now to the drawings wherein like reference numerals are used to identify identical components in the various views, FIG. 2 illustrates one embodiment of an electrophysiology catheter 18 in accordance with the present teachings. Catheter 18 is provided for use in generating an electrophysiological map of tissue and, in particular, cardiac tissue. It should be understood, however, that catheter 18 may be used with tissues other than cardiac tissue. Catheter 18 may include a cable connector or interface 20, a handle 22, a shaft 24 having a proximal end 26 and a distal end 28, and a basket electrode assembly 30. Catheter 18 may also include other conventional components not illustrated herein such as deflection mechanisms, additional electrodes and corresponding conductors or leads.

Connector 20 provides mechanical and electrical connection(s) for cables extending from an electronic control unit (ECU) (not shown) or similar device that is configured to receive signals generated by basket electrode assembly 30. Connector 20 may be conventional in the art and be disposed at the proximal end 26 of catheter 18.

Handle 22 provides a location for the physician to hold catheter 18 and may further provides a means for steering or guiding shaft 24 within the body. For example, handle 22 may include means to change the length of a guide wire extending through catheter 18 to distal end 28 of shaft 24 to steer distal end 28 and, thus, shaft 24. Handle 22 may also be conventional in the art and it will be understood that the construction of handle 22 may vary.

Shaft 24 is an elongate, deformable member configured for movement within the body. Shaft 24 supports electrode assembly 30, associated conductors, and, in some embodiments, additional electronics used for signal processing or conditioning. Shaft 24 may also be configured to permit transport, delivery, and/or removal of fluids (including irrigation fluids and bodily fluids), medicines, and/or surgical tools or instruments. Shaft 24 may be made from conventional materials such as polyurethane and defines one or more lumens configured to house and/or transport electrical conductors, fluids, medicines, guide wires or surgical tools or instruments. Shaft 24 may be introduced into a blood vessel or other structure within the body through an introducer sheath. Shaft 24 may then be steered or guided through the body to a desired location such as tissue in a region of interest using guide wires or pull wires or other means known in the art including remote control guidance systems.

Figure 3:
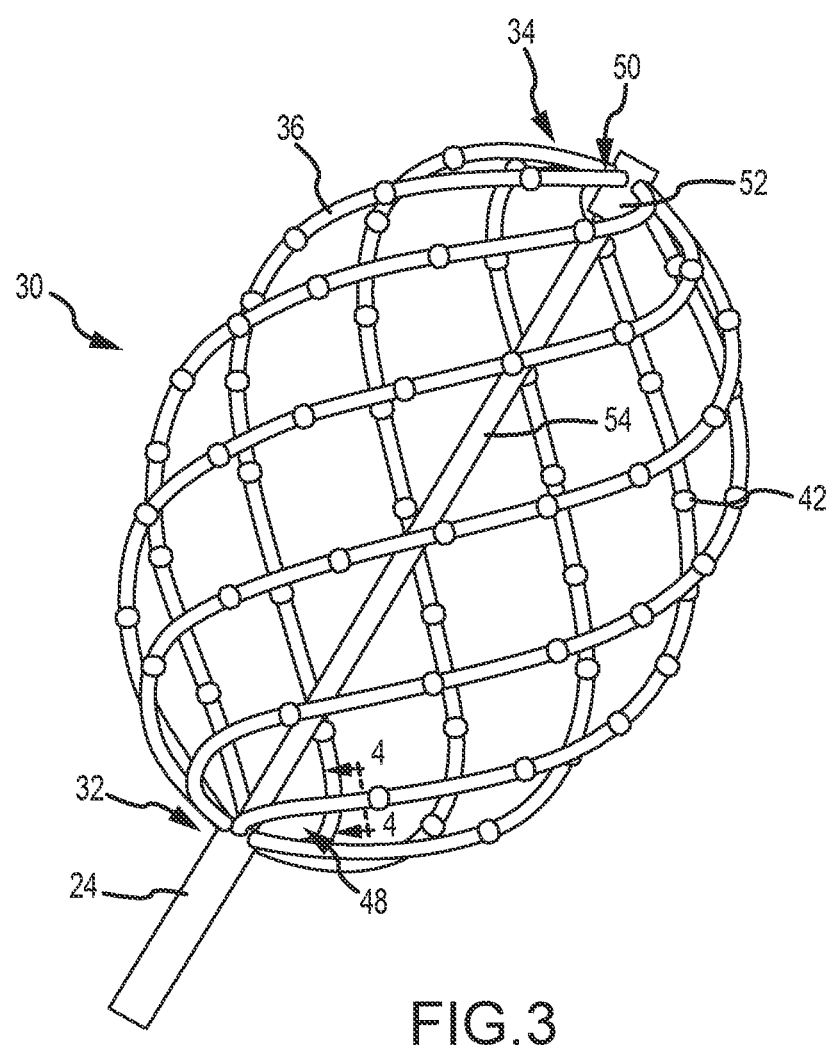
FIG. 3 is an enlarged perspective view of a portion of the electrophysiology catheter of FIG. 2.
Figure 4:
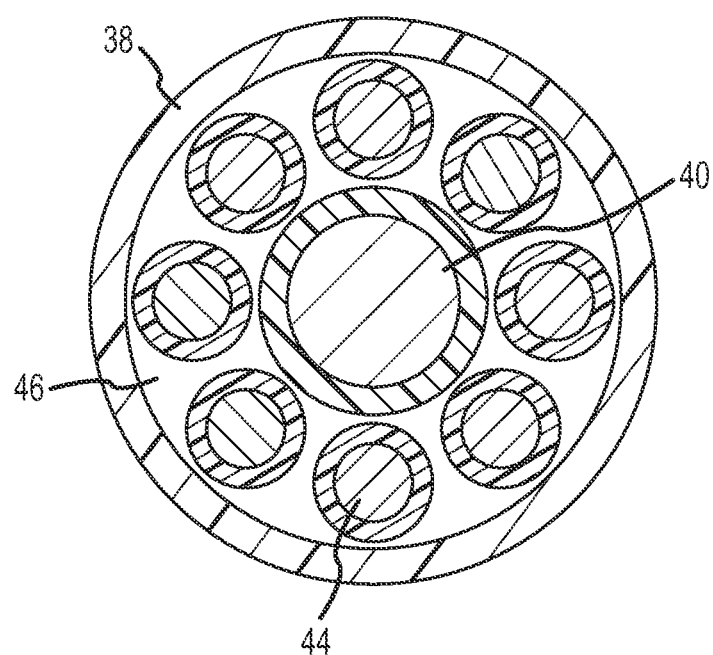
FIG. 4 is a cross-sectional drawing of the electrophysiology catheter of FIG. 3 taken along line 4-4 in FIG. 3.

Referring now to FIGS. 3 and 4, electrode assembly 30 provides a means for conducting an electrophysiological study of tissue. Assembly 30 may be coupled to a distal end of shaft 24 and includes a proximal end 32 and a distal end 34. Assembly 30 may include a plurality of splines 36 on which electrodes are disposed and that form an electrode "basket" that is configured to assume a compressed state and an expanded state. Assembly 30 may assume the expanded state in the absence of an extraneous force acting on the assembly 30 (i.e. assembly 30 may be biased to the expanded state) or may be urged to the expanded state through mechanical means (e.g. wires that are pulled or pushed). Assembly 30 may assume the compressed state, for example, as catheter 18 is maneuvered through an introducer sheath within the body to the region of interest and assume the expanded state upon emerging from a distal end of the sheath. Splines 36 are configured to support electrodes in a predetermined configuration to allow contact and/or non-contact mapping of electrical activity in tissue. Referring to FIG. 4, each spline 36 may include a tubular body 38, means, such as wire 40, for supporting body 38 and biasing body 38 to assume a predetermined shape, one or more electrodes 42 and associated conductors 44. Although a particular embodiment for a spline, e.g., spline 36, is illustrated herein, it should be understood that spline(s) may be constructed in a variety of ways. In one embodiment, for example, one or more splines may include a flexible circuit as described and illustrated in U.S. patent application Ser. No. 12/958,992 (published as United States patent application publication no. 2012/0143298 A1), the entire disclosure of which is incorporated herein by reference. Additional embodiments of splines and/or basket electrode assemblies may be found described in one or more of U.S. States patent application Ser. No. 13/072,357 (published as United States patent application publication no. US 2011/0213231 A1) and U.S. patent application Ser. No. 13/340,760, the entire disclosures of which are incorporated herein by reference.

Body 38 provides structural support for electrodes 42 and insulates conductors 44 from bodily fluids and other elements. Referring to FIG. 4, body 38 is tubular and may be annular in shape. It should be understood, however, that the shape of body 38 may vary. Body 38 may be made from conventional polymeric materials such as polyurethane, and nylon or thermoplastic elastomers such as the elastomer sold under the registered trademark "PEBAX" by Arkema, Inc. and reinforcements such as metallic braids. Body 38 may define a central lumen 46 extending between proximal and distal ends 48, 50 of body 38 and configured to allow passage of wire 40 and conductors 44. It should be understood, however, that body 38 may alternatively define one or more channels each configured to receive one of wire 40 or a conductor 44. In the illustrated embodiment, wire 40 is illustrated at the center of lumen 46 with conductors 44 disposed circumferentially around wire 40. It should be understood, however, that the relative arrangement of wire 40 and conductors 44 within lumen 46 may vary.

Wire 40 is provided to support body 38 and bias body 38 to assume a predetermined shape. Wire may be made from a shape memory alloy such as nitinol (nickel titanium). Wire extends through lumen 46 of body 38 from proximal end 48 of body 38 to distal end 50 and may extend through the bodies 38 of multiple splines 36 to couple one or more splines together. Alternatively, or in addition, splines 36 may be coupled at distal end 50 by a hinge connector 52 or in any of the ways described and illustrated in U.S. patent application Ser. No. 13/340,760 filed Dec. 30, 2011, the entire disclosure of which is incorporated herein by reference. The distal end 34 of the basket electrode assembly 30 may be specialized to form a small, but blunt mechanical connection point so that the distal portion of the catheter 18 may safely be pressed against tissue.

Figure 5:
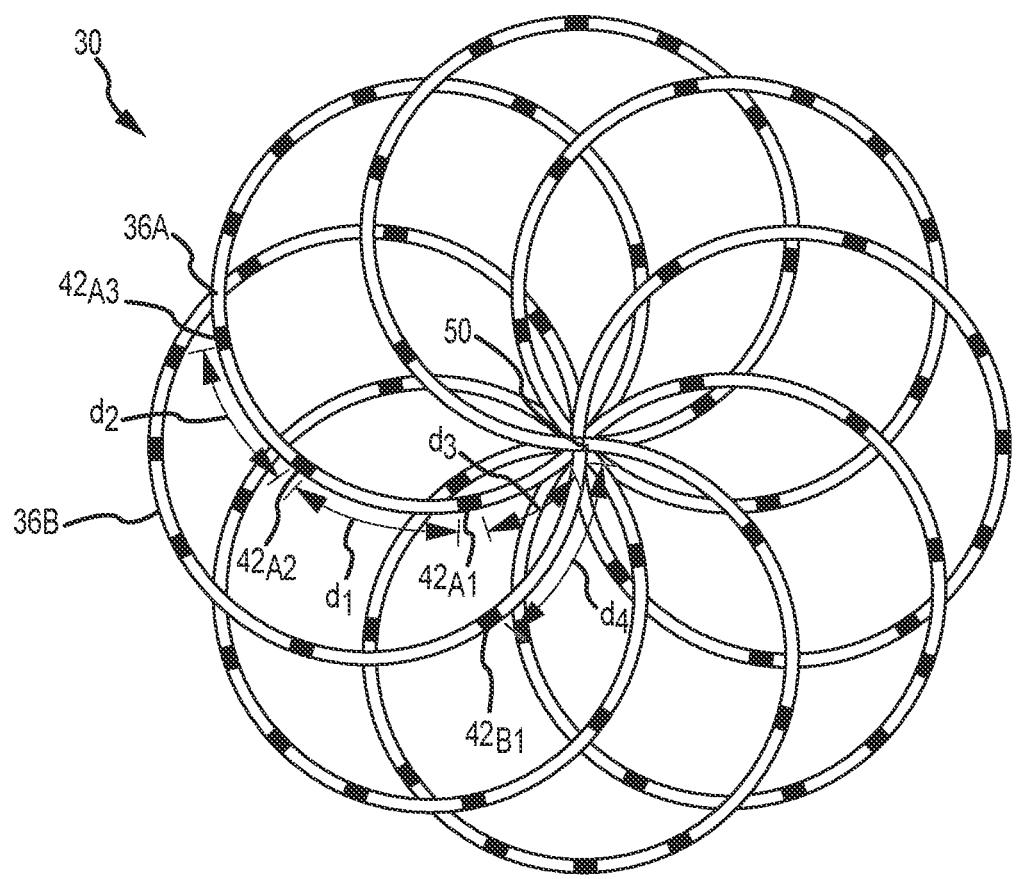
FIG. 5 is a diagrammatic view illustrating the arrangement of the splines of the basket electrode assembly of the catheter of FIG. 3 when the assembly is compressed in the longitudinal direction of the catheter.

Referring again to FIG. 3, electrodes 42 may be configured to diagnose, sense, and measure electrical activity in tissue such as cardiac tissue. One or more of electrodes 42 may also be used to provide ablation therapy to tissue. Electrodes 42 may comprise ring electrodes disposed about body 38 and may be made from platinum or other conductive materials. Each electrode 42 is coupled to a corresponding conductor 44. In accordance with one aspect of the present teachings, electrodes 42 may be unevenly spaced along spline 36. Referring to FIG. 5, for example, the distance $d_1$ between a pair of adjacent electrodes 42 such as electrodes $42_{A1}$, $42_{A2}$, on a spline 36A may be different than a distance $d_2$ between another pair of adjacent electrodes such as electrodes $42_{A2}$, $42_{A3}$ on the same spline 36A. In accordance with one embodiment the distances between adjacent electrodes 42 on a spline 36 may be smallest at or near the midpoint of the spline 36 and increase moving towards the ends of each spline 36. This configuration allows a relatively uniform distribution of the electrodes 42 when the basket electrode assembly 10 is fully expanded. In particular, the spacing between electrodes 42 on adjacent splines 36 is greater near the midpoints of the splines 36 when assembly 10 is in the expanded state and less near the ends of the splines 36 when assembly 10 is in the expanded state. By reducing the spacing between adjacent electrodes 42 on each spline 36 near the midpoints of the spline 36 and increasing the spacing between adjacent electrodes on each spline 36 near the ends of the spline 36, the varied spacing between adjacent electrodes 42 on an individual spline 36 compensates for the relative spacing between electrodes 42 on adjacent splines 36 when assembly 10 is in the expanded state. The placement of electrodes 42 along different splines 36 in assembly 30 may also differ. In particular, a distance $d_3$ between the distal most electrode $42_{A1}$ on a spline 36A and the distal end 50 of spline 36A may differ from a distance $d_4$ between the distal most electrode $42_{B1}$ on another spline 36B and the distal end 50 of spline 36B. Similarly, the distances for corresponding electrodes 42 on splines 36 from either the proximal or distal ends 48, 50 of the splines 36 may vary (such that, for example, the distance between the proximal end 48 of a spline 36 and the third electrode 42 from the proximal end 48 of the spline 36 differs from the distance between the proximal end 48 of another spline 36 and the third electrode 42 from the proximal end 48 of the other spline 36).

Referring again to FIG. 4, conductors 44 may be configured to transmit electrical signals from electrodes 42 through shaft 24 of catheter 18 to an electronic control unit or similar device. Conductors 44 may comprise wires or cables or other means for conducting signals and may be disposed with the lumen 46 of a body 38 of a given spline 36. Each conductor 44 may be coupled at a distal end to a corresponding electrode 42 and extend through lumen 46 to the proximal end 32 of basket electrode assembly 30.

Figure 1:
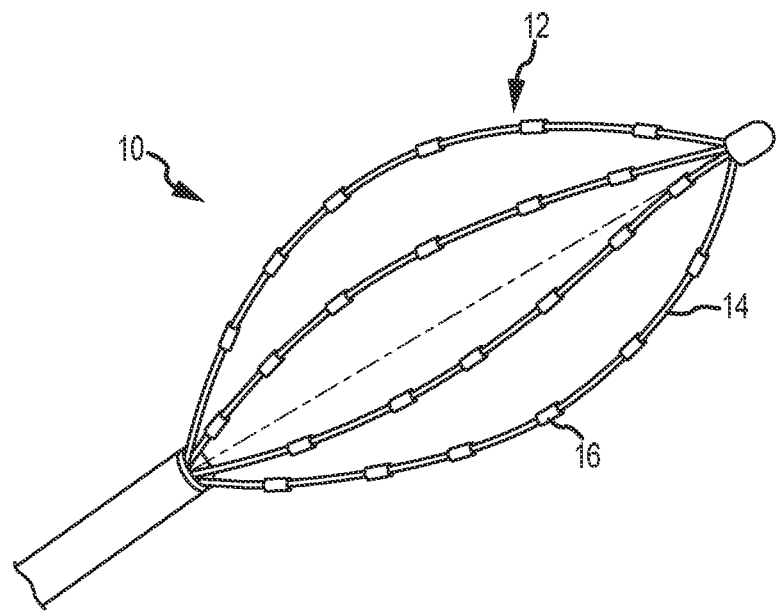
FIG. 1 is a perspective view of a prior art electrophysiology mapping catheter.

As mentioned hereinabove, the body 38 of each spline 36 may be biased to assume a predetermined shape when assembly 30 is in an expanded state. As illustrated in FIG. 3, each of splines 36 can be coupled at the proximal end 32 of basket electrode assembly 30 and a distal end of each spline 36 can be coupled to the connector 52. In the illustrated embodiment, outside of the distal and proximal ends, each of the splines 36 is free floating and uncoupled to surrounding splines. In accordance with one aspect of the present teachings, each of splines 36 may be configured to assume a non-planar shape, such as a twisted shape (e.g., a helical shape), when assembly 30 is in the expanded state. The use of a helical shape, for example, enables a more even distribution of electrodes, and therefore more even sampling of electrical activity in tissue, in both contact and non-contact mapping. The use of a helical shape may also enable controlled shifting of assembly 30 between the compressed and expanded states using, for example, wires that may be pulled or pushed by the physician. In the illustrated embodiment, catheter 18 includes eight helical splines 36. Referring to FIG. 5, when assembly 30 is compressed in the longitudinal direction of assembly 30 and catheter 18, assembly 30 may form a flower-shaped pattern. As a result, the electrodes 42 on splines 36 are dispersed more evenly throughout the pattern and, therefore, dispersed more evenly throughout the area of contact with the tissue as compared to the prior art design in FIG. 1 in which the electrodes 16 are closely spaced near the proximal and distal ends of the splines 14, but relatively distantly spaced near the midpoints of each spline 14 when the assembly 12 in FIG. 1 is compressed in the longitudinal direction. The illustrated catheter 18 may prove useful, for example, in generating a map of a pulmonary vein which is currently done using spiral or hoop electrode assemblies. Similarly, when assembly 30 is compressed laterally due to the contact with tissue (e.g. perpendicular to the longitudinal direction of the catheter), the helical shape of splines 36 reduces the tendency for certain splines nearest the point of contact to move away from one another (and towards other adjacent splines) as in the design illustrated in FIG. 1 because a portion of each spline 36 is located on a diametrically opposite side of the assembly 30 relative to the point of contact. Referring again to FIG. 5, electrodes 42 may be unevenly spaced along each individual spline 36 or located at different relative locations along any two splines as described hereinabove to further facilitate a more even distribution of electrodes 42. One methodology for locating the electrodes 42 on multiple helical splines 36 is to locate an electrode 42 on one spline 36 at a first distance from the end 48 or 50 of the spline 36. The next electrode 42 may be located on a different spline—either adjacent to the first spline 36 or on a non-adjacent spline 36 with the spacing between the splines defining a fixed angle of rotation—at a second distance from the common end 48 or 50 of the splines 36 different than the first distance. Subsequent electrodes 42 may be located on splines 36 by (i) rotating the same fixed angle of rotation relative to the spline 36 having the most recently placed electrode 42 and (ii) increasing the distance from the common end 48 or 50 relative to the spline 36 having the most recently placed electrode 42. Another methodology may involve locating electrodes 42 on a subset of splines 36 (e.g., every other spline 36 as shown in FIG. 5 or another combination of non-adjacent splines 36) at a first distance from the common end 48 or 50 of splines 36 and then locating electrodes 42 on another subset of splines 36 at a second distance from the common end 48 or 50 of splines 36 different than the first distance and locating subsequent electrodes in a similar manner to that described hereinabove.

Referring again to FIG. 3, in accordance with one aspect of the present teachings, catheter 18 may further includes means, such as central post 54, for rotating one end 32, 34 of basket electrode assembly 30 relative to the other end 32, 34, of basket electrode assembly 30. Post 54 may comprise a wire or cable in some embodiments. Post 54 may be rigidly coupled to the distal end 50 of basket assembly 30 and may be coupled to connector 52. Post 54 extends through shaft 24 and may be rotatable relative to shaft 24. Handle 22 may include means, such as a rotary actuator, through which the physician or a robotic controller may cause rotation of post 54 to thereby cause rotation of distal end 34 of assembly 30 relative to the fixed proximal end 32 of assembly 30. In this manner, the physician may control the helical pitch of splines 36, the mechanical stiffness of assembly 30, and the spacing of electrodes 42. Post 54 may move axially relative to shaft 24 so that the length of post 54 will vary with the compression or expansion of basket electrode assembly 30.

Figure 6:
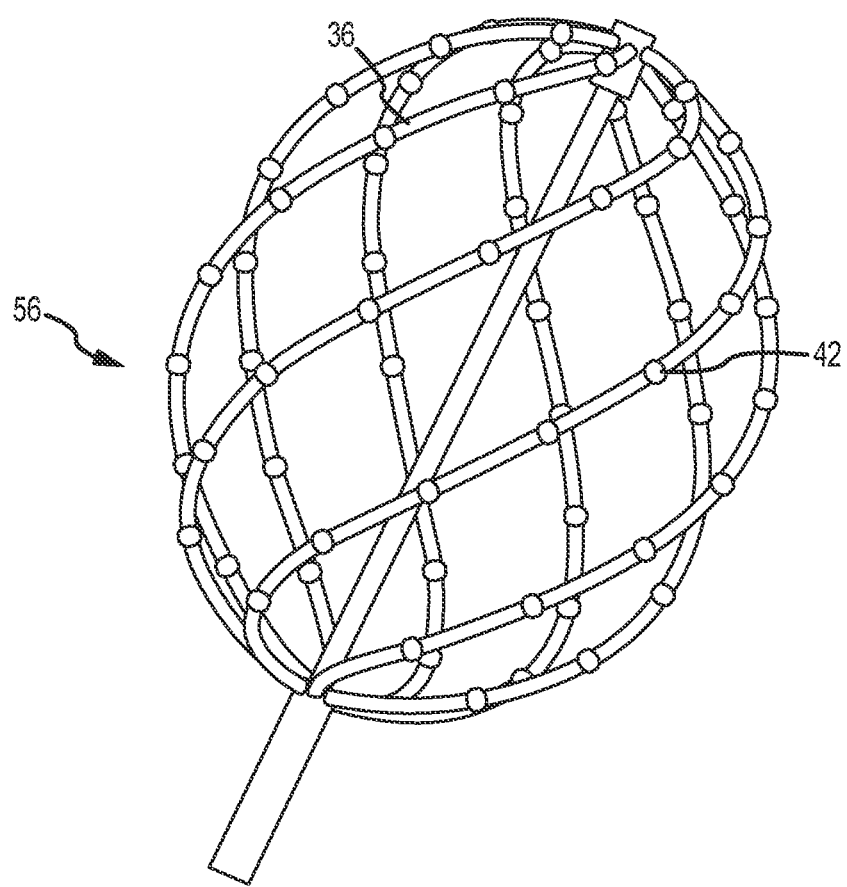
FIG. 6 is an enlarged perspective view of a portion of an electrophysiology catheter in accordance with another embodiment of the present teachings.

As discussed hereinabove, electrodes 42 may be unevenly spaced along splines 36 to achieve a more even distribution of electrodes 42 when assembly 30 is in an expanded state. Referring to FIG. 6, however, an electrophysiology catheter 56 in accordance with another embodiment of the present teachings is illustrated. Catheter 56 is substantially similar to catheter 18, but the electrodes 42 on each spline 36 are evenly spaced along the spline 36 and/or placed at identical locations on each spline 36 such that one, or a limited number, of splines 36 may be used for more efficient manufacture of catheter 56. Although catheter 56 may not achieve the optimal location of electrodes 42 achieved in catheter 18, the use of helical splines 36 on catheter 56 provides an improved distribution of electrodes 42 in contact and non-contact mapping relative to prior art designs. As illustrated in FIG. 6, each of splines 36 can be coupled at a proximal end of each spline 36 and a distal end of each spline 36 to the basket assembly. In the illustrated embodiment, outside of the distal and proximal ends, each of the splines 36 is self-supporting and uncoupled to surrounding splines.

Figure 7:
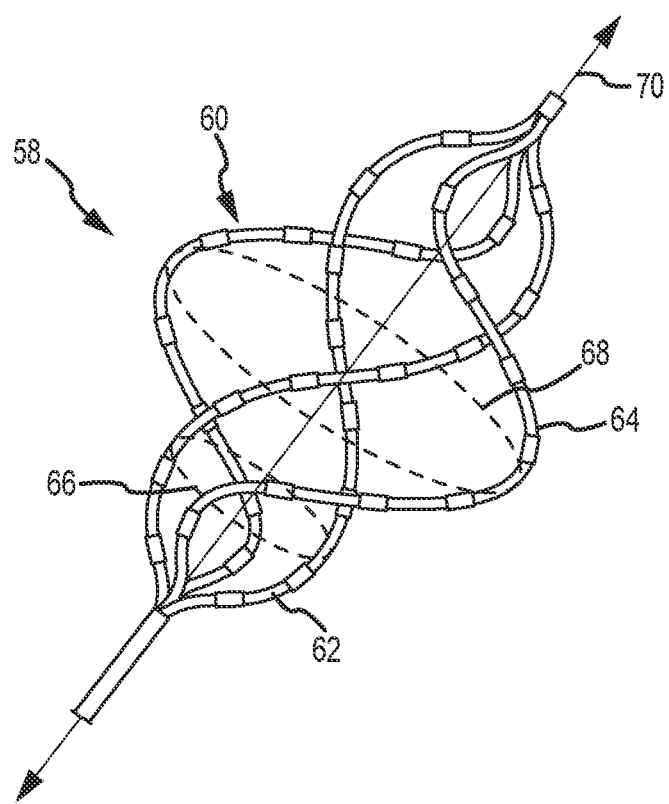
FIG. 7 is an enlarged perspective view of a portion of an electrophysiology catheter in accordance with another embodiment of the present teachings.

In the embodiment illustrated in FIG. 3, each of splines 36 has the same helical pitch. Referring now to FIG. 7, another embodiment of an electrophysiology catheter 58 in accordance with the present teachings is illustrated. Catheter 58 is substantially similar to catheter 18, but includes a different basket electrode assembly 60. As in basket electrode assembly 30 of catheter 18, assembly 60 includes splines 62, 64 configured to assume a helical shape when assembly 60 is in an expanded state. As illustrated in FIG. 7, each of splines 62, 64 can be coupled at a proximal end of each spline 62, 64 and a distal end of each spline 62, 64 to the basket electrode assembly 60. In the illustrated embodiment, outside of the distal and proximal ends, each of the splines 62, 64 is independently supported and uncoupled to surrounding splines. In assembly 60, however, splines 62 have a different helical pitch than splines 64. As a result, splines 62 define one circumferential or spherical envelope (indicated by the dashed line 66) when assembly 60 is in an expanded state while splines 64 define another circumferential or spherical envelope (indicated by the dashed line 68). Stated another way, the maximum radial distance of splines 62 from a central longitudinal axis 70 of basket electrode assembly 60 is different than a maximum radial distance of splines 64 from axis 70 when basket electrode assembly 60 is in an expanded state. Catheter 58 may provide advantages in, for example, non-contact mapping. In particular, lateral contact of assembly 60 with tissue may cause splines 64 to bend and deform from their ideal expanded state—particularly near the midpoint between the proximal and distal ends of the splines 64 which may comprise an important location for sampling electrical activity. Splines 62, however, may maintain their ideal expanded state and continue to provide sampling in the desired location. In the illustrated embodiment, splines 62, 64 rotate about axis 70 in the same direction. In an alternative embodiment, however, splines 62, 64 may rotate about axis 70 in opposite directions. Rotation of splines 62, 64 (through, for example, the use of post 54 shown in FIG. 3) would cause the pitch of one of splines 62, 64 to increase while decreasing its maximum radial distance from axis 70 and would cause the pitch of the other of splines 62, 64 to decrease while increasing its maximum radial distance from axis 70. A basket electrode assembly in accordance with this embodiment would enable a physician to change the distribution of the electrodes with respect to the radius from the centroid of the basket.

Figure 8:
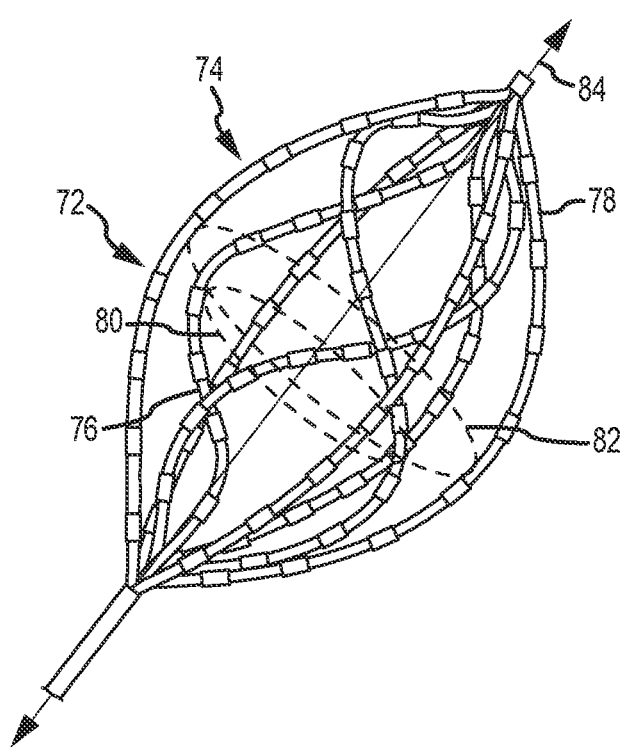
FIG. 8 is an enlarged perspective view of a portion of an electrophysiology catheter in accordance with another embodiment of the present teachings.
Figure 9:
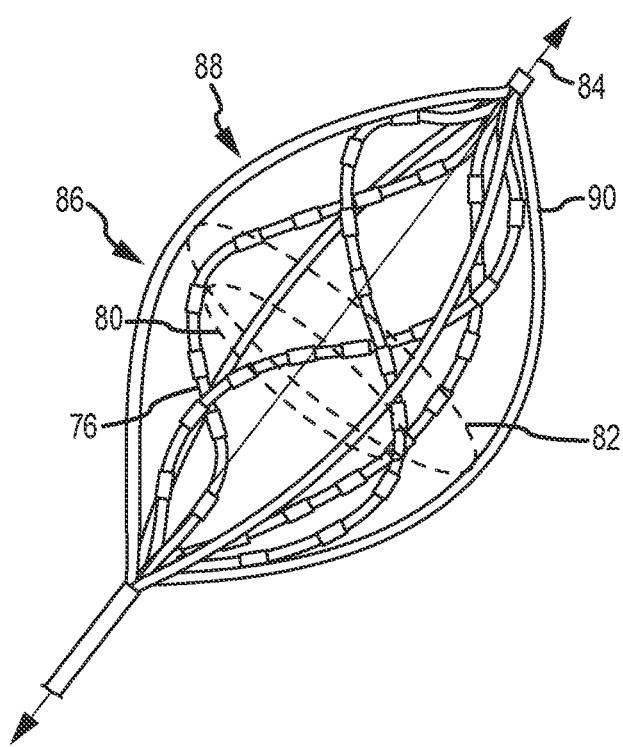
FIG. 9 is an enlarged perspective view of a portion of an electrophysiology catheter in accordance with another embodiment of the present teachings.

Referring now to FIG. 8, another embodiment of an electrophysiology catheter 72 in accordance with the present teachings is illustrated. Catheter 72 is substantially similar to catheters 18 and 58, but includes a different basket electrode assembly 74. As in basket electrode assembly 60 of catheter 58, assembly 74 includes two different types of splines 76, 78. Splines 76 are configured to assume a helical shape when assembly 74 is in an expanded state. Splines 78, however, are configured to assume a shape other than a helical shape when assembly 74 is an expanded state. In particular, splines 78 may assume a bowed "longitude line" or planar shape similar to splines 14 in the embodiment of FIG. 1. Splines 76 and splines 78 again define different circumferential or spherical envelopes 80, 82 when assembly 74 is an expanded state. As shown in the illustrated embodiment, the maximum radial distance of splines 76 from a central longitudinal axis 84 of assembly 74 may be less than the maximum radial distance of splines 78 from axis 84 when assembly 74 is an expanded state. In the embodiment show in FIG. 8, splines 76, 78 both include electrodes. Referring to FIG. 9, another embodiment of an electrophysiology catheter 86 in accordance with the present teachings may be substantially similar to electrophysiology catheter 72, but may include a different basket electrode assembly 88. Assembly 88 is substantially similar to assembly 74, but includes splines 90. Splines 90 are substantially similar to splines 78, but do not include electrodes.

Although several embodiments of a system in accordance with present teachings have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the present teachings as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrophysiology catheter, comprising:
    an elongate, deformable shaft comprising a proximal end and a distal end; and,
    a basket electrode assembly coupled to said distal end of said shaft, said basket electrode assembly comprising a proximal end and a distal end and configured to assume a compressed state and an expanded state and including a plurality of splines comprising a plurality of electrodes disposed thereon;
    wherein each of said plurality of splines are configured to assume a non-planar shape in said expanded state, and wherein the non-planar shape is configured to allow the plurality of electrodes to assume a predetermined configuration,
    wherein said basket electrode assembly is sized and configured to fit within a heart and wherein the plurality of electrodes are spaced between a proximal end and a distal end of each of the plurality of splines and are configured to allow for non-contact mapping of electrical activity in a tissue of the heart, and
    wherein said plurality of splines are free floating.

2. The electrophysiology catheter of claim 1 wherein said non-planar shape comprises a twisted shape.

3. The electrophysiology catheter of claim 2 wherein said twisted shape comprises a helical shape.

4. The electrophysiology catheter of claim 2 wherein a distance from one of the plurality of electrodes on a second of the plurality of splines to said distal end of said basket electrode assembly is different than a distance from any of said plurality of electrodes on a first of the plurality of splines to said distal end of said basket electrode assembly in said expanded state.

5. The electrophysiology catheter of claim 1 wherein a helical pitch of said first spline in said expanded state is different than a helical pitch of said second spline in said expanded state.

6. The electrophysiology catheter of claim 1 wherein one of the plurality of splines is configured to assume a shape other than a helical shape in said expanded state.

7. The electrophysiology catheter of claim 6 wherein a maximum radial distance of one of the plurality of splines from a central longitudinal axis of said basket electrode assembly is different than a maximum radial distance of another of the plurality of splines from said central longitudinal axis when said basket electrode assembly is in said expanded state.

8. The electrophysiology catheter of claim 1 wherein said a distance between first and second electrodes of said plurality of electrodes is different than a distance between second and third electrodes of said plurality of electrodes.

9. The electrophysiology catheter of claim 1 wherein at least one of the plurality of splines is tubular and includes a plurality of conductors, each of said plurality of conductors extending through the at least one of the plurality of splines from a corresponding one of said plurality of electrodes to said proximal end of said basket electrode assembly.

10. The electrophysiology catheter of claim 1, wherein the plurality of electrodes are configured to be dispersed unevenly along each spline to facilitate a more even distribution of electrodes on the basket electrode assembly.

11. The electrophysiology catheter of claim 1, wherein the basket electrode assembly further comprises a spline comprising a planar shape.

12. An electrophysiology catheter, comprising:
    an elongate, deformable shaft comprising a proximal end and a distal end; and,
    a basket electrode assembly coupled to said distal end of said shaft, said basket electrode assembly comprising a proximal end and a distal end and configured to assume a compressed state and an expanded state and including:
        a plurality of first splines, each of said plurality of first splines configured to assume a shape other than a helical shape in said expanded state; and,
        a second spline, said second spline comprising an electrode disposed thereon and configured to assume a helical shape in said expanded state,
        wherein said second spline is coupled to the proximal end and the distal end of the basket electrode assembly, and
        wherein said plurality of first splines and said second spline are self-supporting.

13. The electrophysiology catheter of claim 12 wherein each of said plurality of first splines comprises an electrode disposed thereon.

14. The electrophysiology catheter of claim 12 wherein said basket electrode assembly includes a third spline comprising an electrode disposed thereon wherein said third spline is configured to assume a helical shape in said expanded state and wherein said third spline is self-supporting.

15. The electrophysiology catheter of claim 14 wherein a helical pitch of said second spline in said expanded state is different than a helical pitch of said third spline in said expanded state.

16. The electrophysiology catheter of claim 12 wherein each of said plurality of first splines and said second spline includes:
   a plurality of electrodes disposed thereon; and,
   a plurality of conductors, each of said plurality of conductors extending from a corresponding one of said plurality of electrodes to said proximal end of said basket electrode assembly.

17. The electrophysiology catheter of claim 12 wherein a maximum radial distance of said second spline from a central longitudinal axis of said basket electrode assembly is different than a maximum radial distance of each of said plurality of first splines from said central longitudinal axis when said basket electrode assembly is in said expanded state.

18. An electrophysiology catheter, comprising:
   an elongate, deformable shaft comprising a proximal end and a distal end; and,
   a basket electrode assembly coupled to said distal end of said shaft, said basket electrode assembly comprising a proximal end and a distal end and a central longitudinal axis and configured to assume a compressed state and an expanded state and including:
      a first spline, said first spline comprising an electrode disposed thereon and comprising a first maximum radius relative to said axis in said expanded state; and,
      a second spline, said second spline comprising an electrode disposed thereon and comprising a second maximum radius relative to said axis in said expanded state, said second maximum radius different than said first maximum radius,
      wherein said first spline and said second spline are each coupled to the proximal end and the distal end of the basket electrode assembly and are each independently supported.

19. The electrophysiology catheter of claim 18 wherein at least one of said first and second splines assumes a helical shape in said expanded state.

20. The electrophysiology catheter of claim 18 wherein both of said first and second splines assume a helical shape in said expanded state and a helical pitch of said first spline differs from a helical pitch of said second spline.

21. The electrophysiology catheter of claim 18 wherein each of said first and second splines is tubular and includes
   a plurality of electrodes disposed thereon; and,
   a plurality of conductors, each of said conductors extending from a corresponding one of said plurality of electrodes to said proximal end of said basket electrode assembly.

* * * * *